(12) United States Patent
Murakami

(10) Patent No.: US 9,144,416 B2
(45) Date of Patent: Sep. 29, 2015

(54) ULTRASONIC TREATMENT APPARATUS

(71) Applicant: OLYMPUS CORPORATION, Tokyo (JP)

(72) Inventor: Miyuki Murakami, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 168 days.

(21) Appl. No.: 13/847,134

(22) Filed: Mar. 19, 2013

(65) Prior Publication Data

US 2013/0261461 A1 Oct. 3, 2013

(30) Foreign Application Priority Data

Apr. 2, 2012 (JP) ................................. 2012-083998

(51) Int. Cl.
| | |
|---|---|
| *A61B 8/00* | (2006.01) |
| *A61B 8/08* | (2006.01) |
| *A61B 8/12* | (2006.01) |
| *A61N 7/02* | (2006.01) |
| *A61B 5/04* | (2006.01) |
| *A61B 17/22* | (2006.01) |
| *A61B 18/00* | (2006.01) |
| *A61N 7/00* | (2006.01) |

(52) U.S. Cl.
CPC ................ *A61B 8/4444* (2013.01); *A61B 5/04* (2013.01); *A61B 8/0858* (2013.01); *A61B 8/0883* (2013.01); *A61B 8/12* (2013.01); *A61N 7/02* (2013.01); *A61N 7/022* (2013.01); *A61B 8/445* (2013.01); *A61B 8/5223* (2013.01); *A61B 2017/22008* (2013.01); *A61B 2018/00839* (2013.01); *A61N 2007/0008* (2013.01); *A61N 2007/0021* (2013.01); *A61N 2007/0039* (2013.01); *A61N 2007/0052* (2013.01); *A61N 2007/0065* (2013.01); *A61N 2007/0082* (2013.01); *A61N 2007/0091* (2013.01); *A61N 2007/0095* (2013.01)

(58) Field of Classification Search
CPC ...... A61B 8/4444; A61B 8/0883; A61B 8/12; A61B 8/445; A61N 7/022; A61N 2007/0021; A61N 2007/0008; A61N 2007/0039; A61N 2007/0091; A61N 2007/0095
USPC .................................................. 600/437-469
See application file for complete search history.

(56) References Cited

U.S. PATENT DOCUMENTS

| | | | |
|---|---|---|---|
| 4,886,491 A | | 12/1989 | Parisi et al. |
| 5,840,030 A | * | 11/1998 | Ferek-Petric et al. ........ 600/439 |

(Continued)

FOREIGN PATENT DOCUMENTS

JP Hei 6-20462 3/1994

OTHER PUBLICATIONS

English Abstract of JP 01-262854, dated Oct. 19, 1989 (corresponding to JP Hei 6-20462).

*Primary Examiner* — Sanjay Cattungal
(74) *Attorney, Agent, or Firm* — Scully, Scott, Murphy & Presser, P.C.

(57) ABSTRACT

Arrhythmia is treated with a simple treatment. Provided is an ultrasonic treatment apparatus including a long, thin probe to be inserted into a body, the probe having a contact surface that is brought into contact with tissue in the body and an ultrasonic generating device that radiates ultrasonic waves into the tissue through the contact surface; and a signal detecting portion that is provided at the contact surface of the probe and detects an electrical signal from the tissue. The ultrasonic generating device generates ultrasonic waves focused at a position on the other side of the contact surface from the ultrasonic generating device, the position being away from the contact surface in a direction intersecting the contact surface.

20 Claims, 10 Drawing Sheets

(56) References Cited

U.S. PATENT DOCUMENTS

| | | | |
|---|---|---|---|
| 6,546,934 B1 * | 4/2003 | Ingle et al. | 128/898 |
| 6,558,381 B2 * | 5/2003 | Ingle et al. | 606/41 |
| 6,629,535 B2 * | 10/2003 | Ingle et al. | 128/898 |
| 6,976,492 B2 * | 12/2005 | Ingle et al. | 128/898 |
| 2008/0015569 A1 * | 1/2008 | Saadat et al. | 606/41 |
| 2010/0049186 A1 * | 2/2010 | Ingle et al. | 606/33 |
| 2012/0253338 A1 * | 10/2012 | Sakao et al. | 606/28 |
| 2013/0096471 A1 * | 4/2013 | Slayton et al. | 601/3 |

* cited by examiner

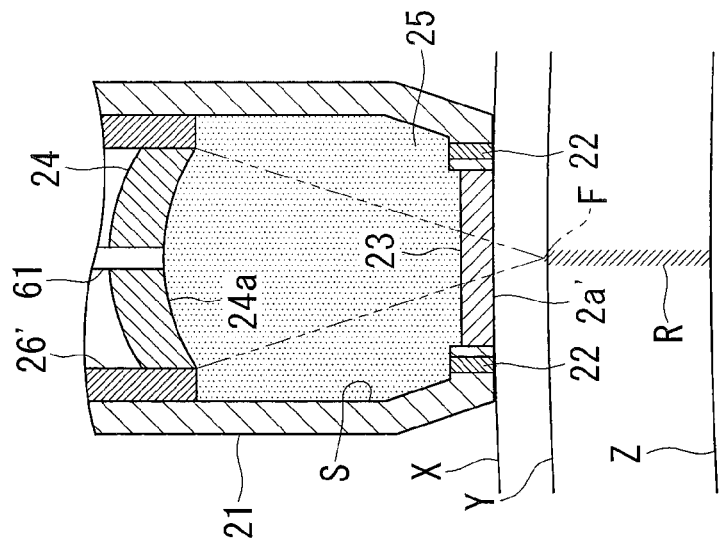
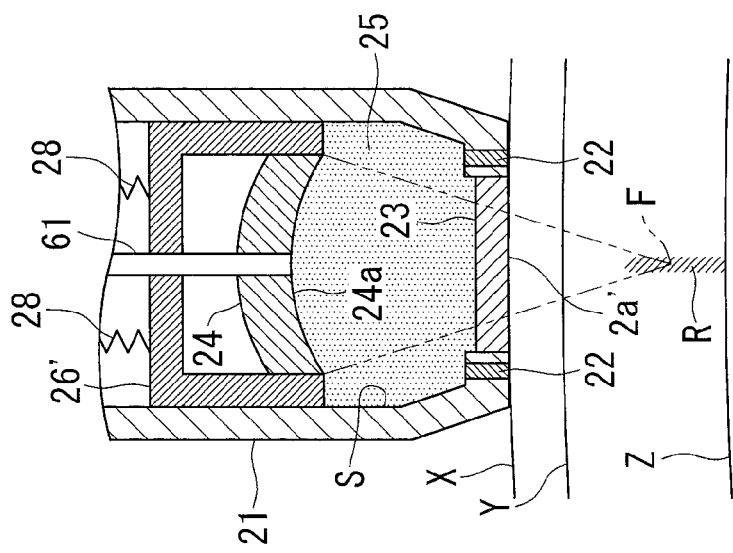
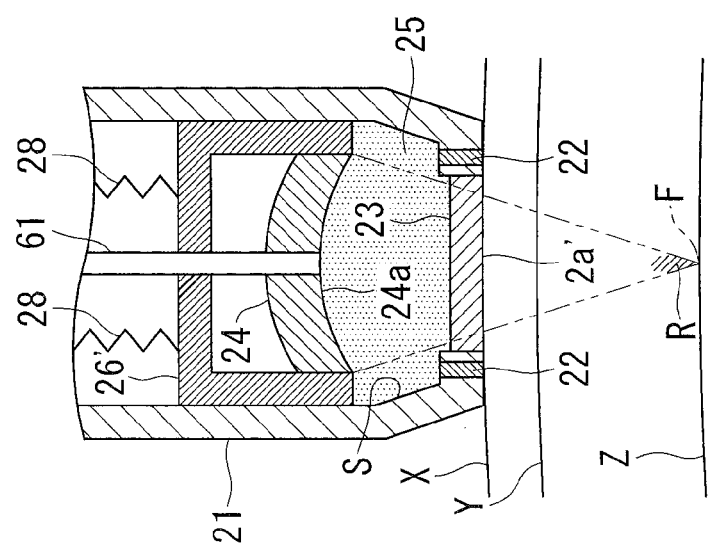

ULTRASONIC TREATMENT APPARATUS

CROSS-REFERENCE TO RELATED APPLICATIONS

This application is based on Japanese Patent Application No. 2012-083998, the content of which is incorporated herein by reference.

TECHNICAL FIELD

The present invention relates to an ultrasonic treatment apparatus.

BACKGROUND ART

An ablation catheter used to treat arrhythmia by cauterizing a portion of cardiac muscle causing arrhythmia with a high-frequency electric current is known. On the other hand, an operation method for externally treating the heart has been proposed, which involves percutaneously inserting a treatment device into a pericardial cavity, which is a space between the heart and the pericardium, from near the xiphisternum. When an ablation catheter is used to cauterize the cardiac muscle from the outside of the heart, the ablation catheter cannot be brought close enough to the cardiac muscle because of fat covering the heart surface, so it is difficult to efficiently supply a high-frequency electric current to the cardiac muscle. To counter this problem, an apparatus for melting and removing fat with ultrasonic waves is used (for example, see PTL 1).

CITATION LIST

Patent Literature

{PTL 1} Japanese Examined Patent Application, Publication No. Hei 6-20462

SUMMARY OF INVENTION

Technical Problem

Because the treatment to melt fat on the heart surface with ultrasonic waves and suck it out of the body using the apparatus disclosed in PTL 1 is complicated, it requires about 30 minutes in open-heart surgery and an even longer time in a percutaneous operation method. Moreover, the operation time becomes even longer when an ablation catheter is inserted into the pericardial cavity for treatment after the apparatus is removed from the body after removal of fat.

Solution to Problem

The present invention provides an ultrasonic treatment apparatus including a long, thin probe to be inserted into a body, the probe having a contact surface that is brought into contact with tissue in the body and an ultrasonic generating device that radiates ultrasonic waves into the tissue through the contact surface; and a signal detecting portion that is provided at the contact surface of the probe and detects an electrical signal from the tissue. The ultrasonic generating device generates ultrasonic waves focused at a position on the other side of the contact surface from the ultrasonic generating device, the position being away from the contact surface in a direction intersecting the contact surface.

BRIEF DESCRIPTION OF DRAWINGS

FIG. 10A shows an area as a result of being cauterized by the ultrasonic treatment apparatus in FIG. 7.

FIG. 10B shows an area as a result of being cauterized by the ultrasonic treatment apparatus in FIG. 7, that is changed from that in FIG. 10A.

FIG. 10C shows an area as a result of being cauterized by the ultrasonic treatment apparatus in FIG. 7, that is changed from that in FIG. 10B.

DESCRIPTION OF EMBODIMENTS

An ultrasonic treatment apparatus 1 according to a first embodiment of the present invention will be described below with reference to FIGS. 1 to 6.

Figure 1:
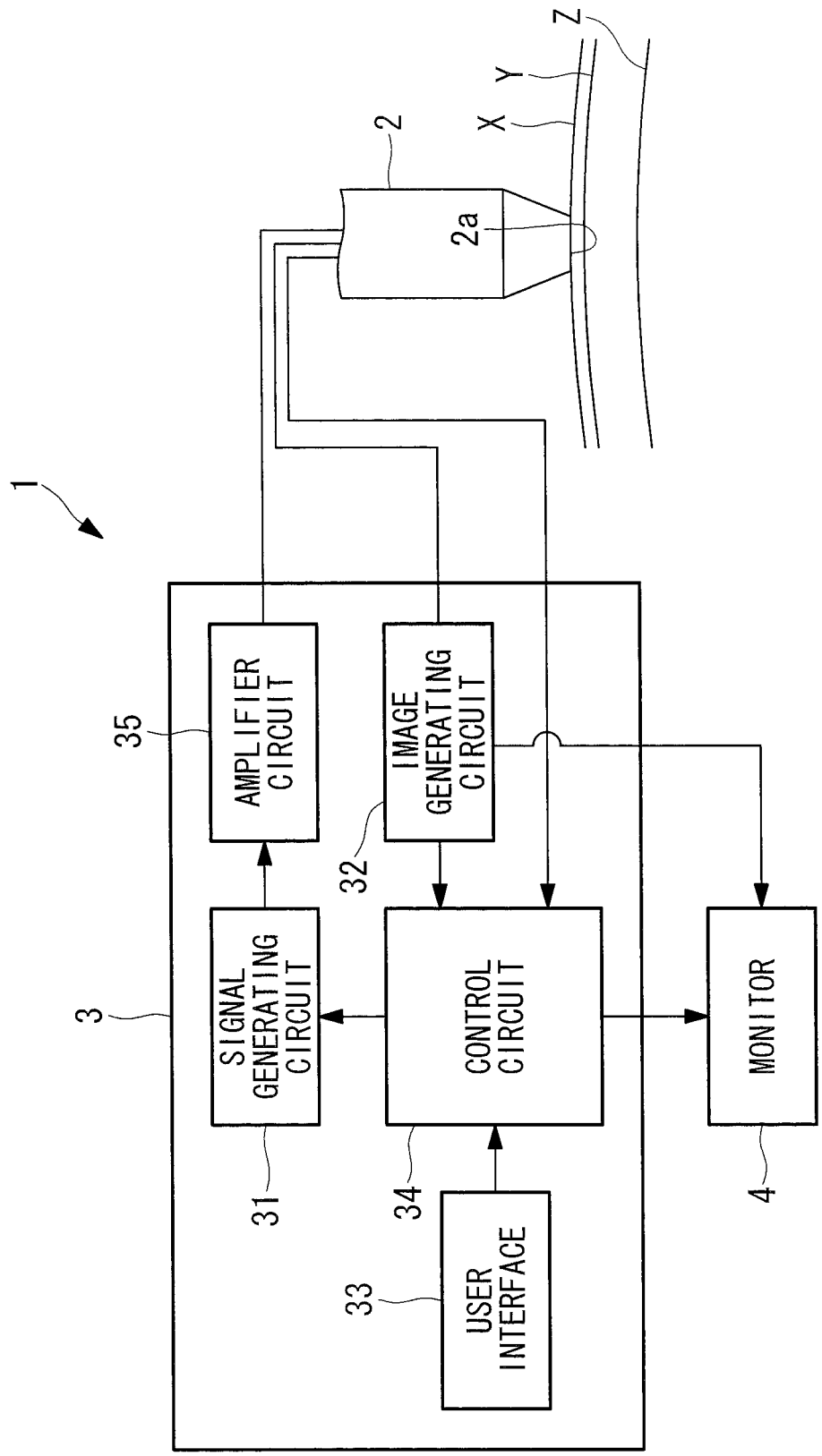
FIG. 1 shows the overall configuration of an ultrasonic treatment apparatus according to a first embodiment of the present invention.

As shown in FIG. 1, the ultrasonic treatment apparatus 1 according to this embodiment includes a probe 2 that is inserted into a body and radiates ultrasonic waves from an end surface (contact surface) 2a, and a control unit 3 and a monitor 4 that are connected to a base end of the probe 2.

Figure 2:
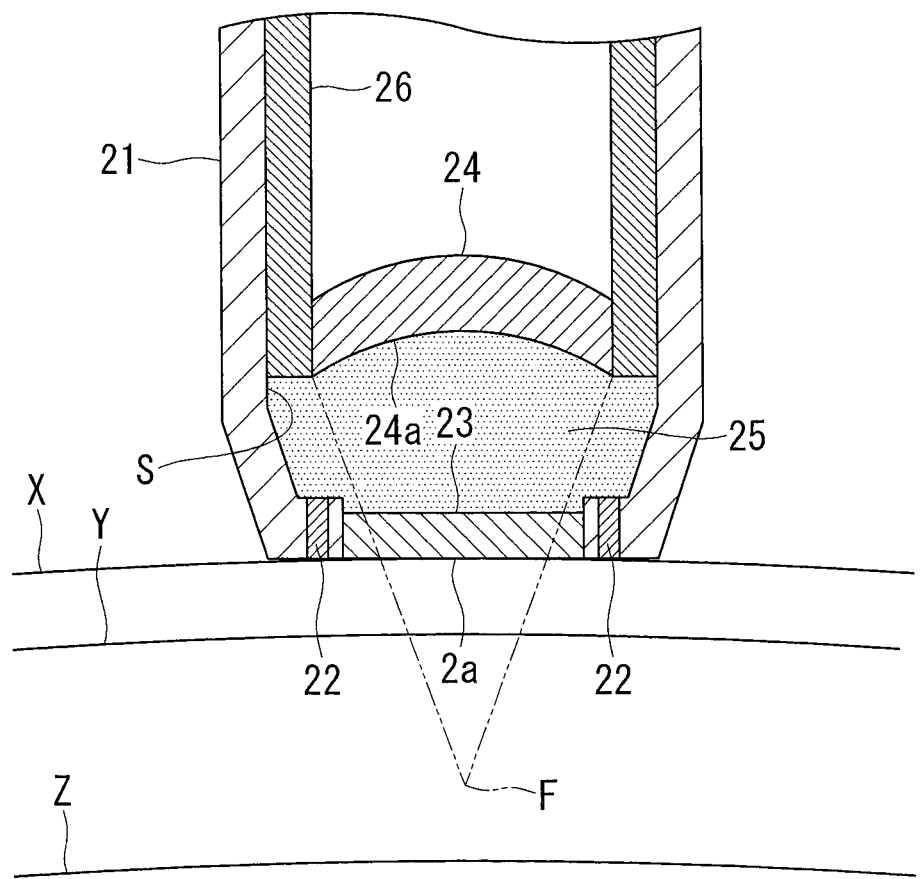
FIG. 2 is an enlarged longitudinal cross-sectional view of a tip of a probe of the ultrasonic treatment apparatus in FIG. 1.

FIG. 2 is a cross-sectional view showing the detailed configuration of a tip of the probe 2. As shown in FIG. 2, the probe 2 includes a long, thin tubular housing 21, electrodes (signal detecting portions) 22 and a window 23 provided at the end surface 2a of the housing 21, an ultrasonic generating device 24 having a concave surface 24a facing the window 23, and an acoustic propagation medium 25 that fills an enclosed space S between the window 23 and the ultrasonic generating device 24. Reference numerals X, Y, and Z denote fat, cardiac muscle, and an atrium or ventricle, respectively.

The housing 21 is flexible and can be bent along the shapes of internal body tissues.

The two electrodes 22 are arranged with the window 23 therebetween. The electrodes 22 detect the local myocardial potential (electrical signal) at a point in the heart (tissue) with which they are in contact. The myocardial potential detected by the electrodes 22 is sent to the control unit 3 and is output to the monitor 4 from the control unit 3. An operator can diagnose if there is an abnormal myocardial potential caused by arrhythmia from a myocardial potential waveform displayed in a time-series manner on the monitor 4.

The window 23 is made of a material that allows ultrasonic waves to pass therethrough and seals a through-hole formed in the end surface 2a of the housing 21.

The ultrasonic generating device 24 generates ultrasonic waves when an alternating-current voltage output from a signal generating circuit 31 (described below) and amplified by an amplifier circuit 35 is applied thereto and radiates the generated ultrasonic waves from the concave surface 24a. The ultrasonic waves radiated from the concave surface 24a are focused at a focal point F. The temperature at the focal point F increases because the ultrasonic energy density is locally increased, and the tissue is cauterized. The position of the focal point F is determined by the shape of the concave surface 24a, and the radius of curvature of the concave surface 24a is designed such that the focal point F is formed at a position outside the window 23 and away from the window 23 in a direction intersecting the surface of the window 23. With this configuration, the ultrasonic waves can be made to locally act on a position away from the window 23.

The ultrasonic generating device 24 alternately outputs treatment ultrasonic waves and image-capturing ultrasonic waves under the control of a control circuit 34 provided in the control unit 3, as will be described below. The frequency of the treatment ultrasonic waves is in the range from several tens of kHz to several tens of MHz. When the frequency of the treatment ultrasonic waves is set to several tens of MHz, the ultrasonic waves are efficiently absorbed by the tissue and cauterize the tissue more efficiently.

The ultrasonic generating device 24 also receives reflected waves (echo) of the image-capturing ultrasonic waves reflected by the tissue and incident thereon through the window 23 and outputs a received echo signal to an image generating circuit 32 provided in the control unit 3.

A space between the outer circumferential surface of the ultrasonic generating device 24 and the inner circumferential surface of the housing 21 is sealed by a holder 26, forming the enclosed space S. The acoustic propagation medium 25 that fills this enclosed space S is a degassed flowable medium in which ultrasonic waves propagate. Wires (not shown) connected to the control unit 3 are disposed in a space formed at a base end of the ultrasonic generating device 24.

The control unit 3 includes the signal generating circuit 31 that generates an alternating-current voltage to be supplied to the ultrasonic generating device 24, the image generating circuit (image capturing portion) 32 that generates an image from the echo received by the ultrasonic generating device 24, a user interface 33 operated by an operator, and the control circuit (radiation control portion) 34 that controls the signal generating circuit 31 according to information input to the user interface 33.

The signal generating circuit 31 generates an alternating-current voltage according to a command signal from the control circuit 34 and outputs the voltage.

The image generating circuit 32 generates an ultrasonic image of the tissue from the echo signal sent from the ultrasonic generating device 24 and outputs the generated ultrasonic image to the monitor 4.

The user interface 33 allows an operator to input the ultrasonic wave settings to be generated by the ultrasonic generating device 24 and an instruction to start or stop radiation of the ultrasonic waves. The information input to the user interface 33 is sent to the control circuit 34.

The control circuit 34 transmits a command signal instructing the signal generating circuit 31 to generate an alternating-current voltage to make the ultrasonic generating device 24 alternately generate the treatment ultrasonic waves and the image-capturing ultrasonic waves according to the settings received from the user interface 33.

The control circuit 34 detects a high echo from the ultrasonic image generated by the image generating circuit 32. A high echo is an echo having higher intensity than a normal echo and is displayed with a higher brightness value than the normal echo in the ultrasonic image. At an interface between normal tissue and cauterized tissue, the reflectance of the ultrasonic waves is high, and the intensity of the echo is high. Hence, the control circuit 34 can determine that the tissue is sufficiently cauterized when a high echo is detected.

More specifically, when the control circuit 34 detects a brightness value that is higher than a predetermined threshold among brightness values in an ultrasonic image, the control circuit 34 determines that the area having that brightness value is a high echo area. The control circuit 34 stops radiation of the ultrasonic waves from the end surface 2a of the probe 2 by stopping generation of the signal by the signal generating circuit 31 when a high echo is detected from a predetermined area designated in advance.

The control circuit 34 also stores the time-series myocardial potential received from the electrodes 22 in a memory circuit (not shown) and displays a waveform that indicates the time-series myocardial potential on the monitor 4.

Figure 3:
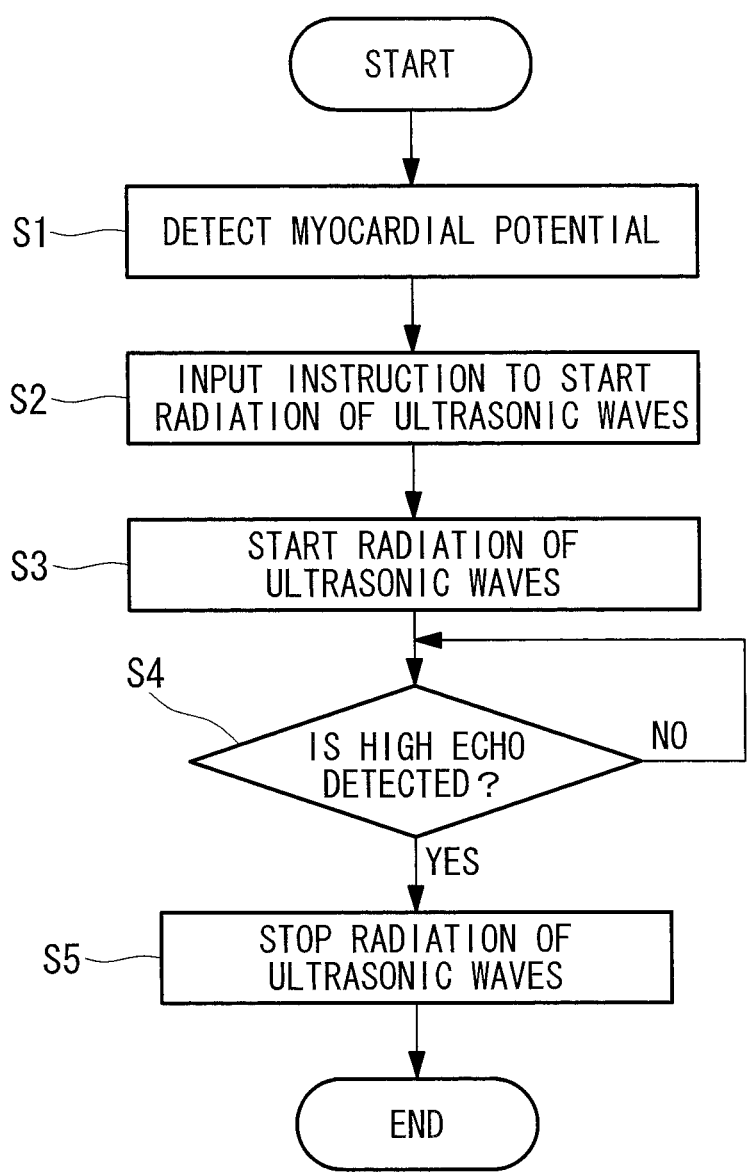
FIG. 3 is a flowchart for explaining the operation of the ultrasonic treatment apparatus in FIG. 1.

Next, the operation of the thus-configured ultrasonic treatment apparatus 1 will be described with reference to the flowchart in FIG. 3.

An operator inserts the probe 2 into the body from, for example, below the xiphisternum, lets the probe 2 pass through the pericardium, and advances the probe 2 into the pericardial cavity, which is a space between the pericardium and the heart. Then, the operator presses the end surface 2a of the probe 2 onto fat X covering the surface of the heart. By doing so, the local myocardial potential is detected by the electrodes 22 (step S1), and a waveform that indicates chronological changes in myocardial potential is displayed on the monitor 4. The operator observes the myocardial potential waveform displayed on the monitor 4 and identifies the position where an abnormal myocardial potential appears. The abnormal myocardial potential appears most distinctively when a site causing arrhythmia is located between the two electrodes 22.

After identifying the site causing arrhythmia, the operator inputs the ultrasonic wave settings to the user interface 33 and inputs an instruction to start radiation of ultrasonic waves (step S2). By doing so, the control circuit 34 activates the ultrasonic generating device 24 (step S3). The treatment ultrasonic waves radiated from the ultrasonic generating device 24 propagate through the fat X and cardiac muscle Y existing below the fat X and are focused at the focal point F located at a position deeper than the surface of the cardiac muscle Y. Due to the cardiac muscle Y absorbing the ultrasonic waves near the focal point F, the cardiac muscle Y is heated and cauterized.

Figure 4A:
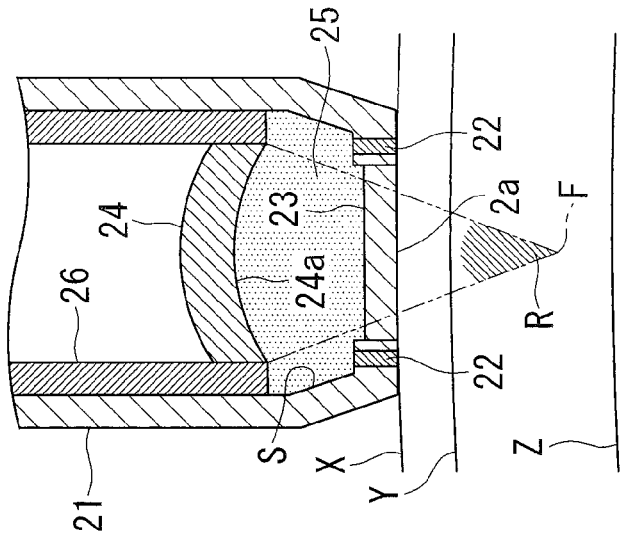
FIG. 4A shows an area as a result of being cauterized by the ultrasonic treatment apparatus in FIG. 1.
Figure 4B:
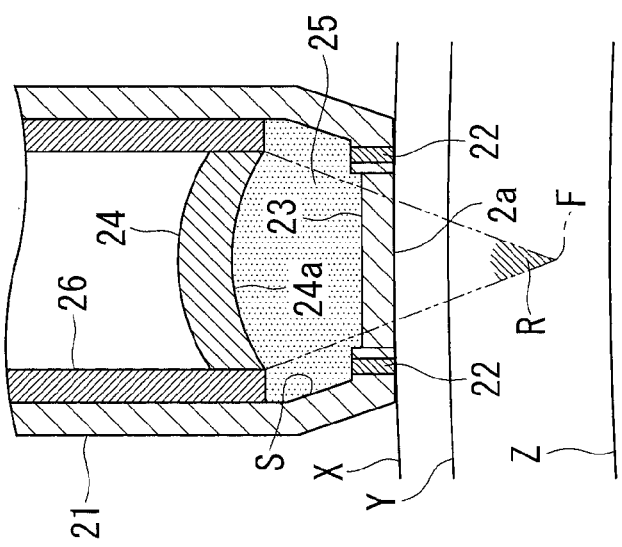
FIG. 4B shows an area as a result of being cauterized by the ultrasonic treatment apparatus in FIG. 1, that is changed from that in FIG. 4A.
Figure 4C:
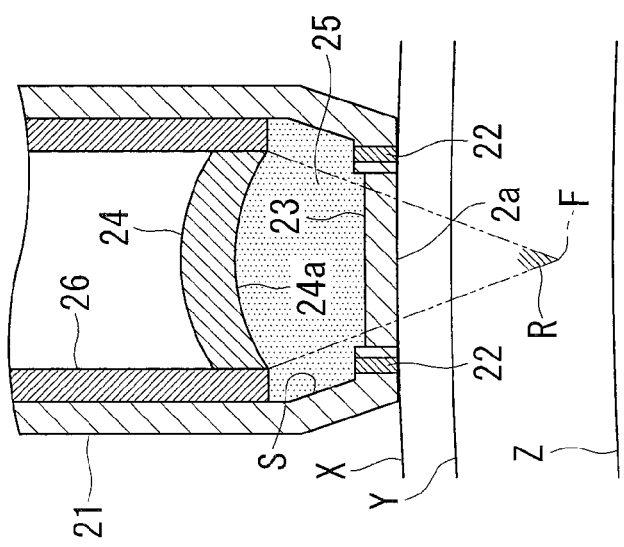
FIG. 4C shows an area as a result of being cauterized by the ultrasonic treatment apparatus in FIG. 1, that is changed from that in FIG. 4B.

Furthermore, due to the treatment ultrasonic waves and the image-capturing ultrasonic waves from the ultrasonic generating device 24 being alternately radiated into the cardiac muscle Y, the image generating circuit 32 generates an ultrasonic image. As shown in FIG. 4A, once the cardiac muscle Y is sufficiently cauterized near the focal point F, a high echo is observed in the ultrasonic image. When the high echo is detected by the control circuit 34 (step S4), radiation of the ultrasonic waves is stopped (step S5). In FIGS. 4A to 4C, reference numeral R denotes a cauterized area.

After radiation of the ultrasonic waves is stopped, the operator confirms that the abnormal myocardial potential has disappeared from the myocardial potential waveform displayed on the monitor 4 and removes the probe 2 from the body. If the abnormal myocardial potential still appears in the waveform, the operator inputs an instruction to start radiation of the ultrasonic waves to the user interface 33 to restart radiation of the ultrasonic waves into the cardiac muscle Y.

If the ultrasonic waves continue to be radiated into the cardiac muscle Y after the cardiac muscle Y near the focal point F is sufficiently cauterized, the cardiac muscle Y at a shallower position than the focal point F will be cauterized. This is because the ultrasonic waves reflected at the interface between the cauterized cardiac muscle Y and the normal cardiac muscle Y act on and cauterize the cardiac muscle Y at a shallower position than the focal point F. Thus, the cauterized area R spreads from the focal point F toward the surface of the cardiac muscle Y, as shown in FIG. 4B. By further continuing radiation of the ultrasonic waves, the cardiac muscle Y can be cauterized up to its surface, as shown in FIG. 4C. The operator observes the myocardial potential waveform on the monitor 4 and stops radiation of the ultrasonic waves via the user interface 33 upon confirming that the abnormal myocardial potential has disappeared.

As has been described above, with this embodiment, by providing the electrodes 22 for detecting the myocardial potential at a portion of the probe 2 that is brought into contact with the cardiac muscle Y with the fat X therebetween, the site causing arrhythmia can be identified with high precision. Furthermore, by employing the configuration in which the ultrasonic waves are focused at the focal point F away from the end surface 2a of the probe 2 so that the ultrasonic waves efficiently act on tissue distant from the end surface 2a, even if the fat X exists between the end surface 2a and the cardiac muscle Y, the ultrasonic waves act on the cardiac muscle Y with sufficiently high efficiency. As a result, removal of the fat X becomes unnecessary, and the treatment can be simplified. Furthermore, in treating arrhythmia, it is desirable to cauterize the cardiac muscle Y in the thickness direction. According to this embodiment, because the cardiac muscle Y can be cauterized in the thickness direction from the focal point F located at a deep portion of the cardiac muscle Y toward the surface of the cardiac muscle Y, sufficient treatment efficacy can be obtained.

Furthermore, because the probe 2 pressed onto the heart is very small, the probe 2 moves with the pulsating heart. In other words, a state in which the probe 2 is stationary with respect to the identified position is maintained. Thus, the treatment can be smoothly performed without needing a separate device for controlling the position of the tip of the probe 2.

Although the operator determines whether to terminate or continue radiation of the ultrasonic waves upon confirming the myocardial potential waveform after the control circuit 34 stops radiation of the ultrasonic waves in this embodiment, instead of this, the control circuit 34 may determine whether to terminate or continue radiation of the ultrasonic waves from the myocardial potential waveform. The control circuit 34 calculates the heart rate from the myocardial potential waveform. If the calculated heart rate is smaller than or equal to a predetermined threshold, radiation of the ultrasonic waves is terminated, and if the calculated heart rate is larger than the predetermined threshold, radiation of the ultrasonic waves is restarted. By doing so, the workload of the operator can be reduced.

Furthermore, although radiation of the ultrasonic waves is stopped when a high echo appears in the ultrasonic image in this embodiment, the criteria for judging whether or not the cardiac muscle Y has been sufficiently cauterized is not limited thereto. For example, a temperature sensor (not shown) may be provided at the end surface 2a of the housing 21, and output of ultrasonic waves may be stopped when the temperature detected by the temperature sensor exceeds a predetermined threshold. Alternatively, a high harmonic component or a subharmonic component contained in the echo of the image-capturing ultrasonic waves may be used as the criteria.

Furthermore, although the control circuit 34 detects a high echo from the ultrasonic image and stops radiation of the ultrasonic waves in this embodiment, instead of this, the operator may input an instruction to stop radiation of the ultrasonic waves to the user interface 33. In this case, the operator may stop the ultrasonic waves when a high echo is observed in the ultrasonic image displayed on the monitor 4, or when the abnormality indicating arrhythmia has disappeared from the myocardial potential waveform displayed on the monitor 4.

Furthermore, the ultrasonic generating device 24 may be composed of a single transducer, as shown in FIG. 2, or it may be composed of a plurality of transducers. For example, the ultrasonic generating device may be composed of a plurality of concentric ring-shaped transducers or a transducer array in which a plurality of chip transducers are arranged in an array.

Figure 5:
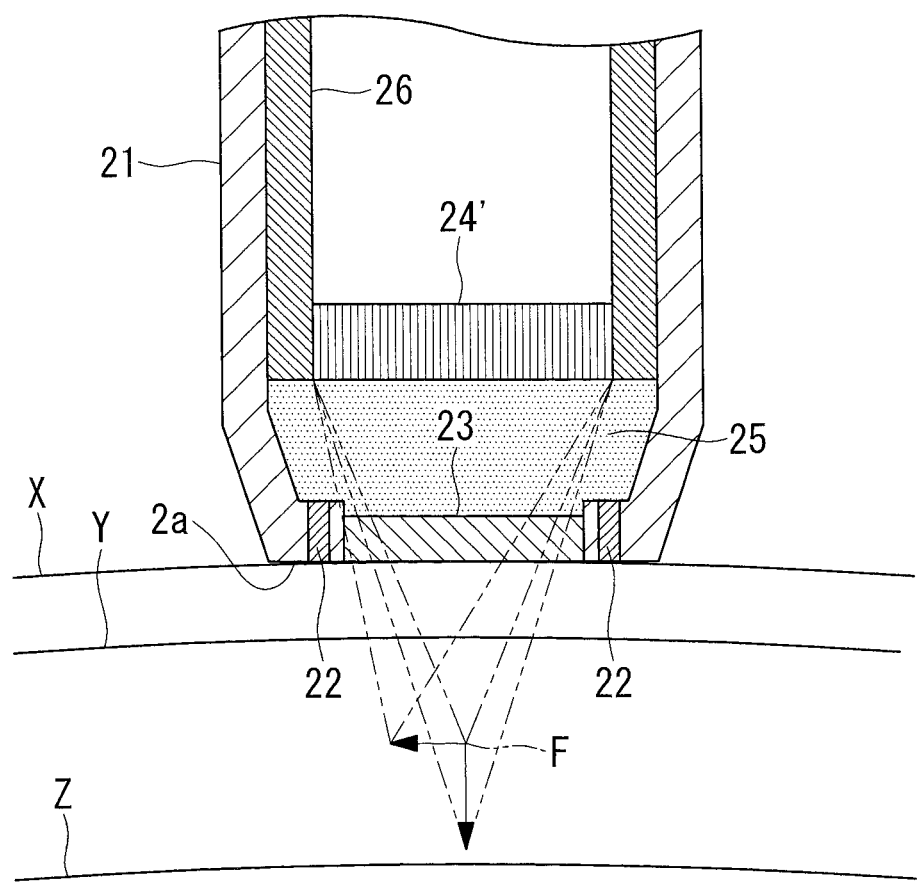
FIG. 5 is an enlarged longitudinal cross-sectional view of a tip of a probe according to a modification of the ultrasonic treatment apparatus in FIG. 1.

As shown in FIG. 5, when an ultrasonic generating device 24' is composed of a transducer array, the ultrasonic waves can be focused at the focal point F by driving the transducers so as to have phase differences. That is, ultrasonic waves focused at the focal point F are generated by applying an alternating-current voltage sequentially with a certain time delay from the transducers arranged on the outer circumferential side to the transducers disposed at the center.

With the configuration in FIG. 5, by adjusting the time delays at which the alternating-current voltage is applied to the transducers, the position of the focal point F can be moved in the depth direction of the cardiac muscle Y (the direction intersecting the end surface 2a) and the direction parallel to the cardiac muscle Y layer (the direction parallel to the end surface 2a). Thus, a larger area can be cauterized while fixing the position of the probe 2 with respect to the heart.

Furthermore, in this embodiment, the ultrasonic generating device 24 may radiate treatment ultrasonic waves formed by combining a plurality of ultrasonic waves having different frequencies. For example, when ultrasonic waves of 5 MHz and ultrasonic waves of 15 MHz are simultaneously radiated, ultrasonic waves of 10 MHz, which corresponds to the difference in frequency between these ultrasonic waves, and ultrasonic waves of 20 MHz, which corresponds to the total frequency of these ultrasonic waves, are generated at the focal point F. By doing so, it is possible to simultaneously cauterize from a deep portion of the cardiac muscle Y to the fat X layer.

Figure 6:
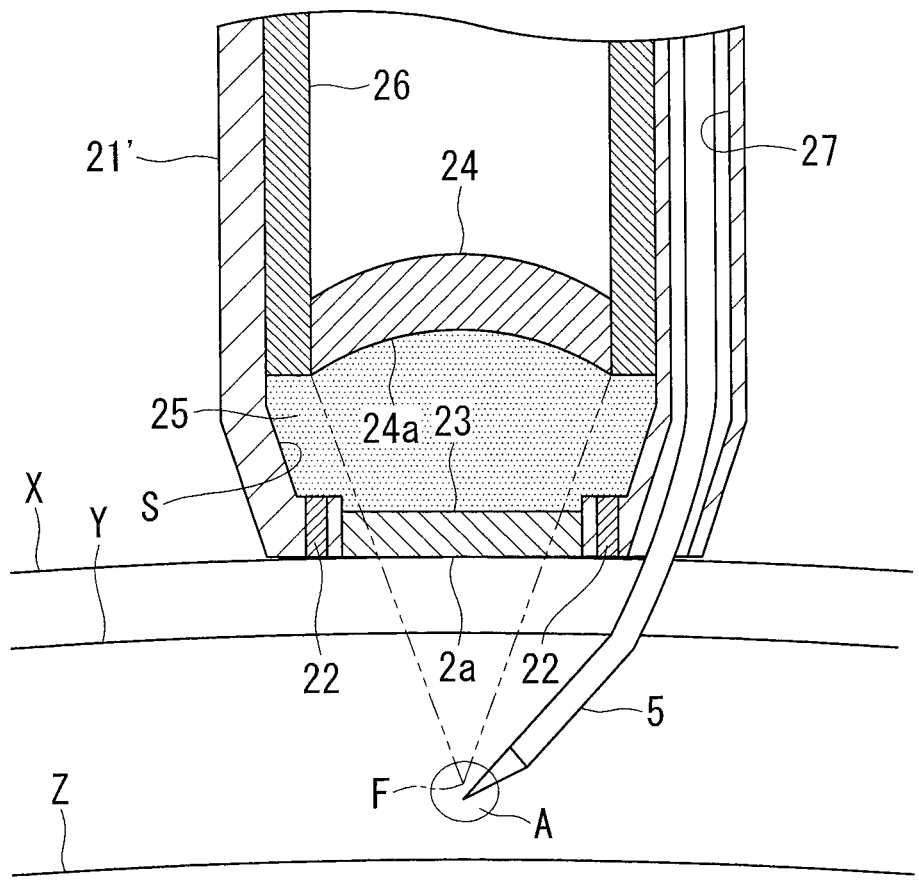
FIG. 6 is an enlarged longitudinal cross-sectional view of a tip of a probe according to another modification of the ultrasonic treatment apparatus in FIG. 1.

Furthermore, in this embodiment, as shown in FIG. 6, a hollow needle 5 and a channel 27, which is provided in the housing 21 in the longitudinal direction and accommodates the needle 5 in the longitudinal direction, may be provided. For example, an end portion of the needle 5 is bent so that the needle point at the end is located near the focal point F in a state in which the end portion protrudes beyond an end opening in the channel 27. A mechanism for limiting the amount of protrusion of the needle 5 from the channel 27 may be provided.

The operator inserts the needle point into the cardiac muscle Y, disposes the needle point near the focal point F, and supplies an ultrasonic contrast medium A to a site near the focal point F through the needle 5. The ultrasonic contrast medium A contains bubbles made from a gas that is insoluble in water and is stabilized by an outer shell, such as a protein, a surfactant, or a lipid. By radiating the ultrasonic waves to the focal point F where these bubbles exist, cavitation is induced at the focal point F, whereby the cauterization efficiency of the cardiac muscle Y can be increased.

Next, an ultrasonic treatment apparatus 1' according to a second embodiment of the present invention will be described with reference to FIGS. 7 to 10C. In this embodiment, the configurations common to those of the ultrasonic treatment apparatus 1 according to the first embodiment will be denoted by the same reference numerals, and descriptions thereof will be omitted. Configurations different from those according to the first embodiment will be mainly described.

Figure 7:
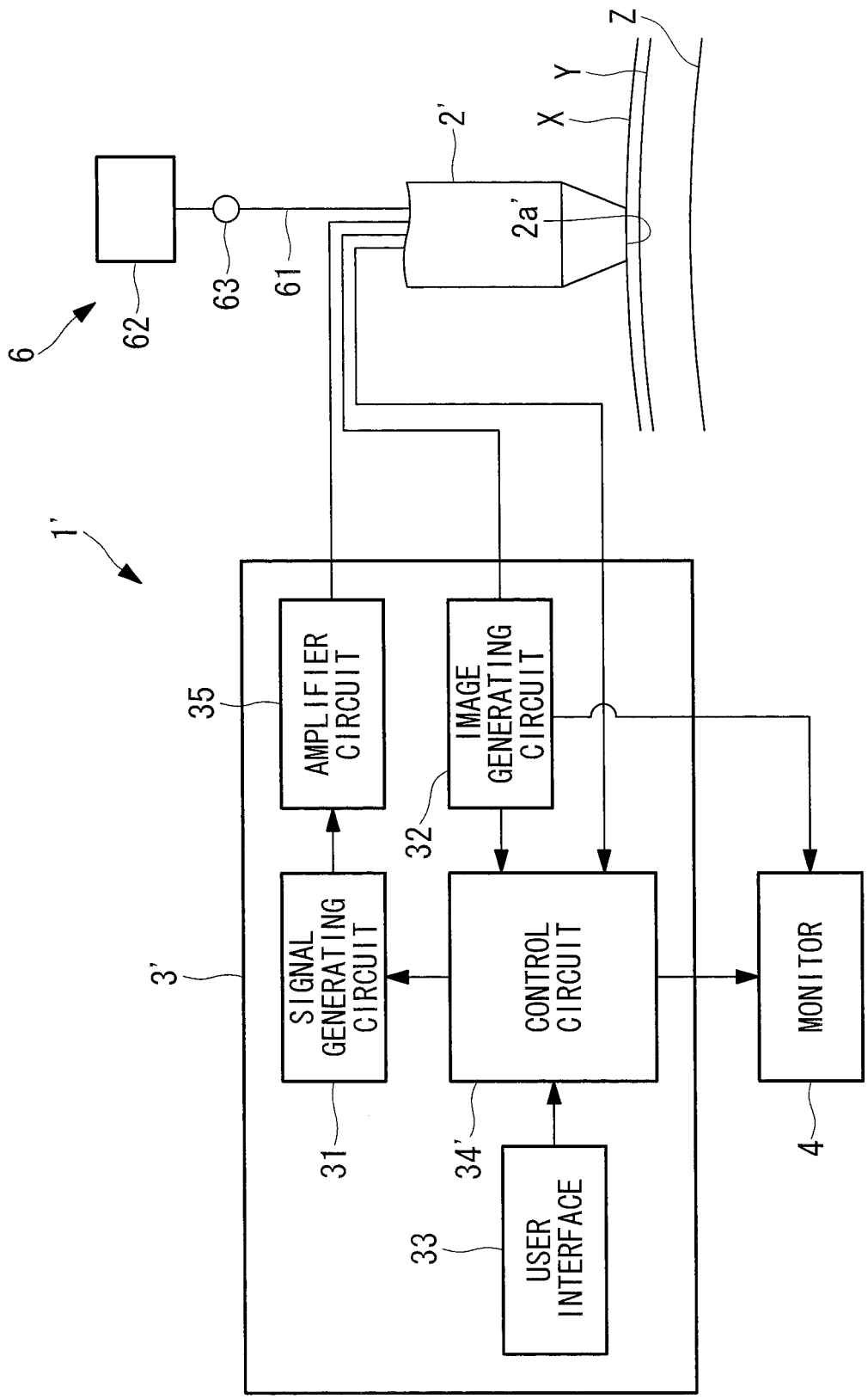
FIG. 7 shows the overall configuration of an ultrasonic treatment apparatus according to a second embodiment of the present invention.
Figure 8:
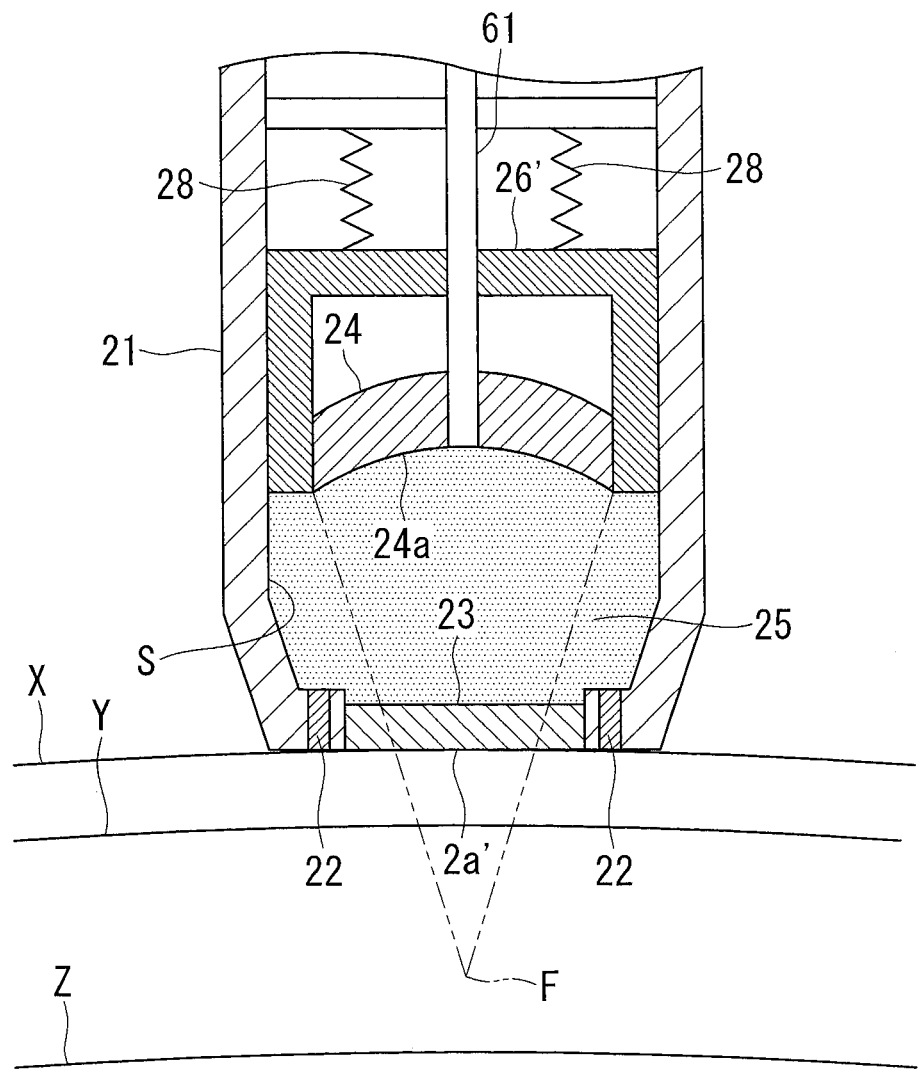
FIG. 8 is an enlarged longitudinal cross-sectional view of a tip of a probe of the ultrasonic treatment apparatus in FIG. 7.

The ultrasonic treatment apparatus 1' according to this embodiment primarily differs from the ultrasonic treatment apparatus 1 according to the first embodiment in that it includes, as shown in FIGS. 7 and 8, an actuator (a driving portion or a focal-point moving mechanism) 28 provided on a probe 2' to move the ultrasonic generating device 24, and a medium-amount adjustment portion 6 that adjusts the amount of the acoustic propagation medium 25 to be filled in the enclosed space S, as well as in the details of the control performed by a control circuit 34'.

The actuator 28 is disposed at a base end of a holder 26' integrated with the ultrasonic generating device 24 and pushes or pulls the holder 26' in the longitudinal direction of the housing 21 to move the ultrasonic generating device 24 in the longitudinal direction of the housing 21. This actuator 28 is made of, for example, a shape-memory alloy. When the ultrasonic generating device 24 is moved in the longitudinal direction of the housing 21, the position of the focal point F of the ultrasonic waves is also moved in the longitudinal direction of the housing 21.

The medium-amount adjustment portion 6 includes a path 61 extending in the housing 21 and communicating between the enclosed space S and the base end of the housing 21, a pump 62 that is connected to the path 61 at the base end of the housing 21 and supplies the acoustic propagation medium 25 to the path 61 or discharges the acoustic propagation medium 25 from the path 61, and a valve 63 that adjusts the amount of liquid passing through the path 61. Although FIG. 8 shows an example configuration in which the end portion of the path 61 penetrates substantially the central portion of the ultrasonic generating device 24 and opens in the enclosed space S, the position at which the path 61 forms an opening in the enclosed space S may be appropriately changed.

The control circuit 34' drives the pump 62 and the valve 63 according to the position to which the actuator 28 moves the ultrasonic generating device 24. More specifically, when the actuator 28 moves the ultrasonic generating device 24 in the direction toward the end surface 2a', the control circuit 34' causes the acoustic propagation medium 25, in an amount corresponding to the amount of movement thereof, to be discharged from the enclosed space S through the path 61. In contrast, when the actuator 28 moves the ultrasonic generating device 24 in the direction away from the end surface 2a', the control circuit 34' causes the acoustic propagation medium 25, in an amount corresponding to the amount of movement thereof, to be supplied to the enclosed space S through the path 61. Thus, the enclosed space S formed between the window 23 and the ultrasonic generating device 24 is always filled with the acoustic propagation medium 25.

Furthermore, the control circuit (thickness measuring portion) 34' calculates the initial position of the focal point F by the following method and activates the actuator 28 and the medium-amount adjustment portion 6 to locate the focal point F at the calculated initial position.

First, the control circuit 34' causes the ultrasonic generating device 24 to output a single, pulsed ultrasonic wave serving as an ultrasonic wave for measuring the thickness of the cardiac muscle Y, and analyzes an echo received by the ultrasonic generating device 24. Because more ultrasonic waves are reflected at the interface between substances, the echo received by the ultrasonic generating device 24 contains peaks corresponding to the interface between the window 23 and the fat X, the interface between the fat X and the cardiac muscle Y, and the interface between the cardiac muscle Y and the atrium or the ventricle Z. The control circuit 34' measures the time intervals between these peaks and calculates the thicknesses of the fat X and the cardiac muscle Y using the measured time intervals. Then, the control circuit 34' calculates the deepest position in the cardiac muscle Y as the initial position of the focal point F.

In addition, the control circuit 34' causes treatment ultrasonic waves and image-capturing ultrasonic waves to be alternately radiated, with the focal point F being set to the initial position. Then, after detecting a high echo from the ultrasonic image, the control circuit 34' stops radiation of the ultrasonic waves, drives the actuator 28 and the medium-amount adjustment portion 6 to move the position of the focal point F toward the end surface 2a' by a predetermined distance, and restarts radiation of the ultrasonic waves. The control circuit 34' repeats detection of a high echo, stopping of the ultrasonic waves, movement of the focal point F, and radiation of the ultrasonic waves until the position of the focal point F reaches the surface of the fat X.

Figure 9:
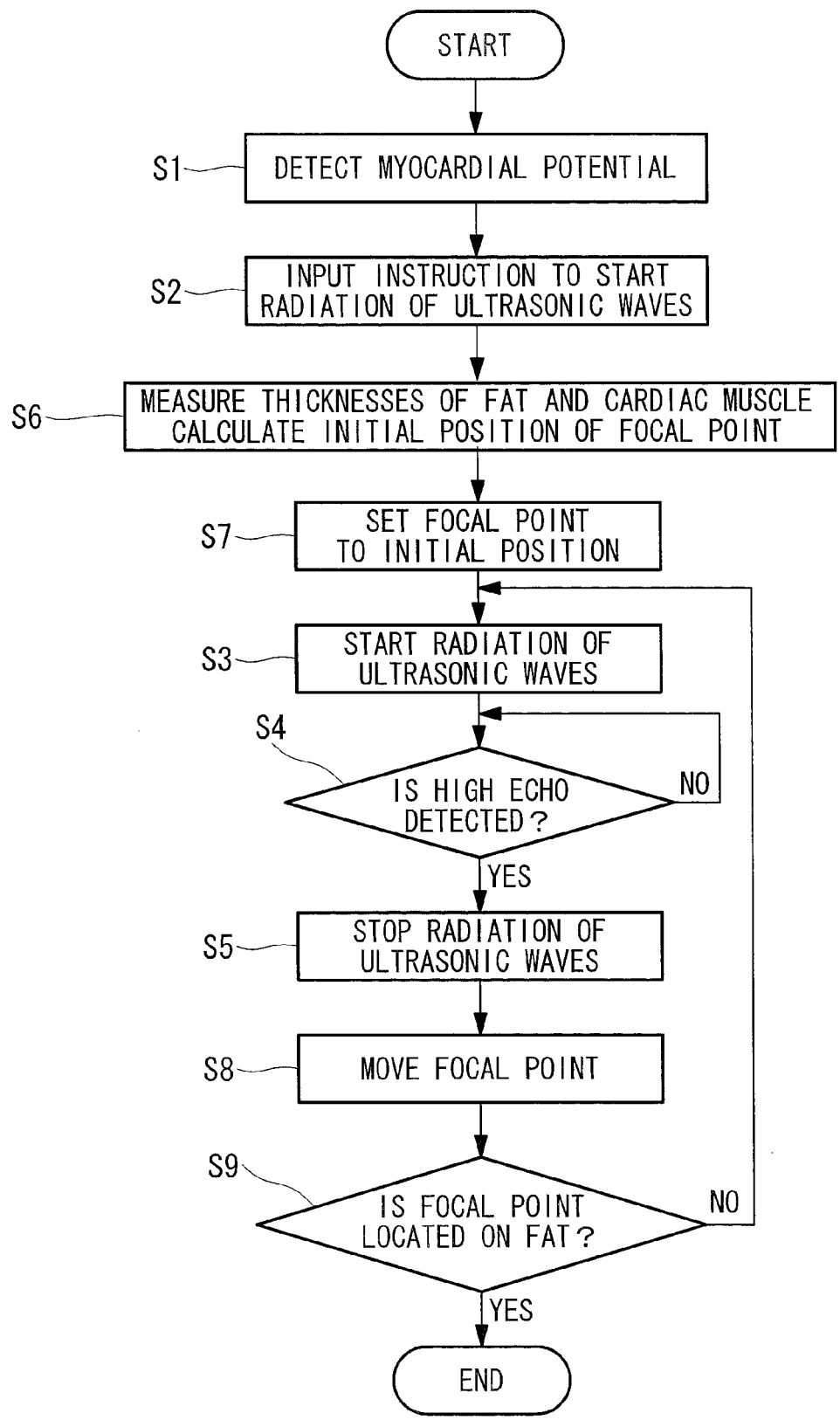
FIG. 9 is a flowchart for explaining the operation of the ultrasonic treatment apparatus in FIG. 7.

Next, the operation of the thus-configured ultrasonic treatment apparatus 1' will be described with reference to the flowchart in FIG. 9.

The ultrasonic treatment apparatus 1' according to this embodiment is operated in the same way as that according to the first embodiment, until the site causing arrhythmia is identified.

After the site causing arrhythmia is identified, the operator inputs to the user interface 33 an instruction to start radiation of ultrasonic waves (step S2). Upon reception of this instruction, the control circuit 34' first measures the thicknesses of the fat X and the cardiac muscle Y (step S6) and drives the actuator 28 and the medium-amount adjustment portion 6 to locate the focal point F at the deepest position in the cardiac muscle Y (step S7). After the focal point F is set to the initial position, the control circuit 34' drives the ultrasonic generating device 24 to start radiation of treatment and image-capturing ultrasonic waves (step S3).

As shown in FIG. 10A, when the cardiac muscle Y is sufficiently cauterized at the focal point F, and a high echo appears in the ultrasonic image (step S4), the control circuit 34' temporarily stops the output of ultrasonic waves (step S5), moves the focal point F by a predetermined distance to a shallower portion in the cardiac muscle Y (step S8), and restarts the output of ultrasonic waves (step S3). Due to the control circuit 34' repeating a series of these operations (steps S3, S4, S5, and S8), as shown in FIG. 10B, the cardiac muscle Y is cauterized sequentially from the deepest position toward a shallow position, and finally, as shown in FIG. 10C, the surface of the cardiac muscle Y is cauterized (step S9).

If a relatively shallow position in the cardiac muscle Y is cauterized first, it is difficult to cause the ultrasonic waves to act on and cauterize the cardiac muscle Y located at a position deeper than the cauterized portion, because the ultrasonic waves are reflected at the interface between the cauterized tissue and the normal tissue. On the other hand, in order to completely treat arrhythmia, it is important to cauterize a portion of the cardiac muscle Y producing an abnormal myocardial potential, over the entire extent in the thickness direction. Herein, according to this embodiment, the cardiac muscle Y can be reliably cauterized over the entire extent in the thickness direction by repeating cauterization while changing the position of the focal point F of the ultrasonic waves little by little from the deepest position to the shallow position in the cardiac muscle Y. Accordingly, this embodiment provides an advantage that arrhythmia can be reliably treated, in addition to the advantage achieved by the first embodiment.

Furthermore, when the ultrasonic waves continue to be radiated with the position of the focal point F being fixed, as shown in FIGS. 4A to 4C, the cauterized area R spreads in the layer direction of the cardiac muscle Y as it gets close to the end surface 2a and has a substantially inverted triangle shape in cross-section of the tissue. On the other hand, as shown in FIG. 10A to FIG. 10C, when the position of the focal point F is gradually moved toward the end surface 2a', the width of the cauterized area R is substantially constant. Accordingly, this embodiment provides an advantage that the cauterized area R can be minimized.

Although the focal point F of the ultrasonic waves is moved by moving the ultrasonic generating device 24 composed of a single transducer with the actuator 28 in this embodiment, instead of this, the focal point F may be moved by providing the ultrasonic generating device 24' composed of the transducer array, as shown in FIG. 5, and controlling the time delays at which an alternating-current voltage is applied to the respective transducers with the control circuit 34'. In this case, the medium-amount adjustment portion 6 is unnecessary, and so the configuration is simplified.

Furthermore, the ultrasonic treatment apparatuses 1 and 1' according to the above-described first and second embodiments may be used to treat diseases accompanying an abnormal signal other than arrhythmia. For example, they may be used to cauterize a site in the brain producing an abnormal brain wave, to cauterize a site in the spinal cord forming an abnormal signal circuit, and to perform cauterization to relief cancerous and chronic pains.

From the embodiments described above, the following invention is derived.

A first aspect of the present invention is an ultrasonic treatment apparatus including a long, thin probe to be inserted into a body, the probe having a contact surface that is brought into contact with tissue in the body and an ultrasonic generating device that radiates ultrasonic waves into the tissue through the contact surface; and a signal detecting portion that is provided at the contact surface of the probe and detects an electrical signal from the tissue. The ultrasonic generating device generates ultrasonic waves focused at a position on the other side of the contact surface from the ultrasonic generating device, the position being away from the contact surface in a direction intersecting the contact surface.

According to the first aspect of the present invention, due to the ultrasonic waves generated by the ultrasonic generating device being radiated into the tissue in contact with the contact surface, the tissue is cauterized. Because the signal detecting portion detects an electrical signal from the tissue in contact with the contact surface, it is possible to identify an affected site producing an abnormal electrical signal, to cauterize the tissue in the identified affected site, and to treat arrhythmia etc.

In this case, because the ultrasonic waves radiated from the contact surface into the tissue are focused at the focal point located at a position away from the contact surface and effectively act on the focal point, even if the surface of the tissue is covered by fat, the tissue is effectively cauterized. Thus, treatment to remove the fat becomes unnecessary, and arrhythmia can be treated by a simple treatment.

In the above-described first aspect, the ultrasonic treatment apparatus may further include a focal-point moving mechanism that moves a focal point, where the ultrasonic waves are focused, in the direction intersecting the contact surface; and a focal-point-position control portion that controls the position to which the focal point is moved by the focal-point moving mechanism.

With this configuration, the position to which the focal point of the ultrasonic waves is moved by the focal-point moving mechanism can be controlled by the focal-point-position control portion.

In the above-described configuration, the ultrasonic treatment apparatus may further include an acoustic propagation medium that fills a space between the ultrasonic generating device and the contact surface and through which the ultrasonic waves propagate, the focal-point moving mechanism may include a driving portion that moves the ultrasonic generating device in the direction intersecting the contact surface and a medium-amount adjustment portion that supplies or discharges the acoustic propagation medium, and the focal-point-position control portion may cause the medium-amount adjustment portion to supply or discharge the acoustic propagation medium in an amount corresponding to the distance by which the ultrasonic generating device is moved by the driving portion.

With this configuration, the ultrasonic generating device is moved in a direction toward or away from the contact surface by the driving portion, and the focal point can be moved in the direction intersecting the contact surface. At this time, due to the amount of movement of the ultrasonic generating device and the amount of the acoustic propagation medium supplied or discharged by the medium-amount adjustment portion being synchronously controlled by the focal-point-position control portion, the space between the ultrasonic generating device and the contact surface is kept filled with the acoustic propagation medium.

In the above-described configuration, the focal-point moving mechanism may include a transducer array in which a plurality of transducers facing the contact surface are arranged in an array, and the focal-point-position control portion may drive the plurality of transducers such that their phases are different.

With this configuration, due to the focal-point-position control portion controlling the phase differences between the transducers when the transducer array is driven so as to have phase differences, the focal point of the ultrasonic waves radiated from the transducer array can be moved in the direction intersecting the contact surface.

In the above-described configuration, the focal-point-position control portion may control the focal-point moving mechanism such that the focal point is gradually moved in a direction toward the contact surface.

With this configuration, by gradually moving the focal point toward the contact surface, the portion to be cauterized is gradually moved from a deep position to a shallow position, and thus, the tissue can be cauterized in the depth direction.

In the above-described configuration, the ultrasonic treatment apparatus may further include a thickness measuring portion that measures the thickness of the tissue in the direction intersecting the contact surface. The focal-point-position control portion may control the focal-point moving mechanism such that the focal point is moved to a most distant position from the contact surface in the direction intersecting the contact surface, on the basis of the thickness of the tissue measured by the thickness measuring portion.

With this configuration, by starting cauterization after locating the focal point at a deepest position in the tissue, the tissue can be cauterized from the deepest position to a shallow position over the entire extent in the thickness direction.

In the above-described first aspect, the ultrasonic treatment apparatus may further include an image capturing portion that captures an image of the tissue, on the basis of reflected waves of the ultrasonic waves radiated from the ultrasonic generating device into the tissue.

With this configuration, an ultrasonic image of the affected site can be observed.

In the above-described first aspect, the ultrasonic treatment apparatus may further include a radiation control portion that stops radiation of the ultrasonic waves from the ultrasonic generating device when a brightness value higher than a predetermined threshold is detected in the image captured by the image capturing portion.

With this configuration, by utilizing the tendency that the reflectance of the ultrasonic waves is high at the cauterized tissue and the brightness value of the reflected waves is high in the image captured by the image capturing portion, the radiation control portion can stop radiation of the ultrasonic waves upon confirming that the tissue has been sufficiently cauterized.

In the above-described first aspect, the ultrasonic generating device may receive reflected waves of the ultrasonic waves radiated into the tissue, and the image capturing portion may capture the image, on the basis of the reflected waves received by the ultrasonic generating device.

With this configuration, by using the same ultrasonic generating device both to generate and to receive the ultrasonic waves, the configuration can be simplified and the diameter of the probe can be reduced.

A second aspect of the present invention is a method of operating an ultrasonic treatment apparatus including an ultrasonic generating device that generates ultrasonic waves focused at a position in the body with a contact surface, which is brought into contact with tissue, located therebetween, and a focal-point moving mechanism that moves a focal point, at which the ultrasonic waves are focused, in a direction intersecting the contact surface, the method comprising gradually moving the focal point in a direction toward the contact surface with the focal-point moving mechanism.

REFERENCE SIGNS LIST 1, 1': ultrasonic treatment apparatus
2, 2': probe
2a: end surface (contact surface)
3: control unit
4: monitor
5: needle
6: medium-amount adjustment portion (focal-point moving mechanism)
21: housing
22: electrode (signal detecting portion)
23: window
24: ultrasonic generating device
24a: concave surface
25: acoustic propagation medium
26, 26': holder
27: channel
28: actuator (driving portion, focal-point moving mechanism)
31: signal generating circuit
32: image generating circuit (image capturing portion)
33: user interface
34: control circuit (focal-point-position control portion, radiation control portion)
35: amplifier circuit
61: path
62: pump
63: valve
A: ultrasonic contrast medium
F: focal point
S: enclosed space
X: fat
Y: cardiac muscle
Z: atrium or ventricle

The invention claimed is:

1. An ultrasonic treatment apparatus comprising:
a probe comprising:
   a contact surface configured to be brought into contact with an intermediate layer of biological substance disposed between the contact surface and a biological tissue;
   an electrode device arranged to the contact surface, wherein the electrode device is configured to detect electrical signals in a portion of the biological tissue, and
   an ultrasonic generating device arranged to the contact surface, wherein the ultrasonic generating device is configured to generate ultrasonic waves focused at one or more positions in the biological tissue set at one or more predetermined distances from the contact surface; and
a control circuit configured to:
   control the electrode device to detect a first electrical signal from the portion of the biological tissue;
   determine whether the first electrical signal detected by the electrode device is of a predetermined type, wherein the predetermined type corresponds to a predetermined condition of the portion of the biological tissue; and
   control the ultrasonic generating device to generate first treatment ultrasonic waves based on a determination that the first electrical signal detected by the electrode device is of the predetermined type.

2. The ultrasonic treatment apparatus according to claim 1, wherein the ultrasonic generating device is configured to generate the first treatment ultrasonic waves at a plurality of frequencies simultaneously such that ultrasonic waves corresponding to a difference in the plurality of frequencies and ultrasonic waves corresponding to a total in the plurality of frequencies are simultaneously applied to a region of the biological tissue extending from a first point set at a first predetermined distance from the contact surface to a second point set at a second predetermined distance from the contact surface, the second predetermined distance being less than the first predetermined distance, to increase the ultrasonic energy density in the region of the biological tissue between the first point and the second point, and
wherein the control circuit is configured to control the ultrasonic generating device to generate the first treatment ultrasonic waves at the plurality of frequencies simultaneously based on the determination that the first electrical signal detected by the electrode device is of the predetermined type to increase the ultrasonic energy density in the region of the biological tissue between the first point and the second point.

3. The ultrasonic treatment apparatus according to claim 1, wherein the control circuit is configured to control the ultrasonic generating device to generate the first treatment ultrasonic waves in the portion of the biological tissue based on the determination that the first electrical signal detected by the electrode device is of the predetermined type, and wherein the control circuit is configured to control the ultrasonic generating device to focus the first treatment ultrasonic waves at a first focal point in the portion of the biological tissue set a first predetermined distance from the contact surface to locally increase the ultrasonic energy density in a first region of the biological tissue including the first focal point.

4. The ultrasonic treatment apparatus according to claim 3, wherein the control circuit is further configured to:

after the generation of the first treatment ultrasonic waves, control the electrode device to detect a second electrical signal from the portion of the biological tissue;

determine whether the second electrical signal detected by the electrode device is of the predetermined type; and control the ultrasonic generating device to generate second treatment ultrasonic waves in the portion of the biological tissue based on a determination that the second electrical signal detected by the electrode device is of the predetermined type.

5. The ultrasonic treatment apparatus according to claim 4, wherein the generation of the first treatment ultrasonic waves locally increases the ultrasonic energy density in the first region of the biological tissue to cauterize the first region of the biological tissue, and wherein the control circuit is configured to control the ultrasonic generating device to generate the second treatment ultrasonic waves to be focused at the first focal point in the portion of the biological tissue such that the second treatment ultrasonic waves are reflected at an interface between the first region in the biological tissue and a second region of the biological tissue that is closer to the contact surface than the first region to locally increase the ultrasonic energy density in the second region of the biological tissue to cauterize the second region of the biological tissue.

6. The ultrasonic treatment apparatus according to claim 4, wherein the control circuit is configured to control the ultrasonic generating device to focus the second treatment ultrasonic waves at a second focal point in the portion of the biological tissue set a second predetermined distance from the contact surface, the second predetermined distance being less than the first predetermined distance, to locally increase the ultrasonic energy density in a second region of the biological tissue including the second focal point.

7. The ultrasonic treatment apparatus according to claim 6, wherein the ultrasonic generating device comprises a plurality of ultrasonic transducers, and wherein the control circuit is configured to control the plurality of ultrasonic transducers to focus the first treatment ultrasonic waves at the first focal point and to control the plurality of ultrasonic transducers to focus the second treatment ultrasonic waves at the second focal point.

8. The ultrasonic treatment apparatus according to claim 7, wherein the plurality of ultrasonic transducers is a plurality of concentric ring-shaped transducers.

9. The ultrasonic treatment apparatus according to claim 7, wherein the plurality of ultrasonic transducers is a plurality of chip transducers arranged in an array.

10. The ultrasonic treatment apparatus according to claim 6, wherein the ultrasonic generating device comprises a radiating surface configured to radiate the first treatment ultrasonic waves and to radiate the second treatment ultrasonic waves, wherein the probe further comprises an actuator configured to:

move the radiating surface relative to the contact surface to focus the first treatment ultrasonic waves at the first focal point; and move the radiating surface relative to the contact surface to focus the second treatment ultrasonic waves at the second focal point, and wherein the control circuit is configured to:

control the actuator to move the radiating surface relative to the contact surface to focus the first treatment ultrasonic waves at the first focal point; and control the actuator to move the radiating surface relative to the contact surface to focus the second treatment ultrasonic waves at the second focal point.

11. The ultrasonic treatment apparatus according to claim 10, wherein the ultrasonic generating device further comprises:

a window arranged to the contact surface, wherein the window and the radiating surface define an enclosed space, and wherein a volume of the enclosed space is changed as a result of the movement of radiating surface by the actuator; and an acoustic propagation medium provided in the enclosed space, wherein the acoustic propagation medium is configured to propagate the ultrasonic waves radiated from the radiating surface, wherein the probe further comprises a medium volume adjusting mechanism configured to supply the acoustic propagation medium to the enclosed space or to discharge the acoustic propagation medium from the enclosed space, and wherein the control circuit is further configured to control the medium volume adjusting mechanism to supply the acoustic propagation medium to the enclosed space or to discharge the acoustic propagation medium from the enclosed space in an amount corresponding to a change in the volume of the enclosed space resulting from the movement of the radiating surface by the actuator.

12. The ultrasonic treatment apparatus according to claim 4, wherein the first treatment ultrasonic waves are set at one or more frequencies sufficient to cauterize the first region of the biological tissue, wherein the ultrasonic generating device is further configured to:

generate image-capturing ultrasonic waves directed at the first region of the biological tissue; and receive reflected waves of the image-capturing ultrasonic waves, and wherein the control circuit is configured to:

determine whether the first region of the biological tissue is cauterized based on the reflected waves of the image-capturing ultrasonic waves; and control the ultrasonic generating device to stop generating the first treatment ultrasonic waves based on a determination that the first region of the biological tissue is cauterized.

13. The ultrasonic treatment apparatus according to claim 3,
further comprising a temperature sensor configured to sense a temperature of the portion of the biological tissue,
wherein the control circuit is configured to:
determine whether the temperature sensed by the temperature sensor exceeds a predetermined temperature threshold; and
control the ultrasonic generating device to stop generating the first treatment ultrasonic waves based on a determination that the temperature sensed by the temperature sensor exceeds the predetermined threshold.

14. The ultrasonic treatment apparatus according to claim 1, further comprising a hollow needle configured:
to be protruded from the contact surface and inserted into the biological tissue; and
to supply an ultrasonic contrast medium to the one or more positions in the biological tissue such that the ultrasonic contrast medium supplied to the one or more positions in the biological tissue increases cauterization efficiency of the ultrasonic waves focused at the one or more positions.

15. The ultrasonic treatment apparatus according to claim 1,
further comprising a user interface configured to receive an input from a user to start generation of the ultrasonic waves focused at the one or more positions,
wherein the control circuit is configured to control the ultrasonic generating device to generate the first treatment ultrasonic waves based on the input from the user to start generation of the ultrasonic waves and the determination that the first electrical signal detected by the electrode device is of the predetermined type.

16. The ultrasonic treatment apparatus according to claim 15,
wherein the user interface is further configured to receive an input from the user to stop generation of the ultrasonic waves focused at the one or more positions, and
wherein the control circuit is configured to stop generation of the first treatment ultrasonic waves based on the input from the user to stop generation of the ultrasonic waves focused at the one or more positions.

17. The ultrasonic treatment apparatus according to claim 1,
wherein the biological tissue is a cardiac muscle of a heart,
wherein the probe further comprises an elongated housing configured to be passed through a pericardium and guided into a pericardial cavity between the pericardium and the heart, and
wherein the contact surface of the probe is arranged to a tip of the elongated housing.

18. The ultrasonic treatment apparatus according to claim 1,
wherein the ultrasonic generating device comprises a plurality of ultrasonic transducers, and
wherein the control circuit is configured to control the plurality of ultrasonic transducers to focus the ultrasonic waves at the one or more positions in the biological tissue set at the one or more predetermined distances from the contact surface.

19. The ultrasonic treatment apparatus according to claim 18, wherein the plurality of ultrasonic transducers is a plurality of concentric ring-shaped transducers.

20. The ultrasonic treatment apparatus according to claim 18, wherein the plurality of ultrasonic transducers is a plurality of chip transducers arranged in an array.

\* \* \* \* \*